(12) United States Patent
Schiffer et al.

(10) Patent No.: US 10,575,390 B2
(45) Date of Patent: Feb. 25, 2020

(54) COLOR SENSING USING PULSED LIGHT

(71) Applicant: Verily Life Sciences LLC, South San Francisco, CA (US)

(72) Inventors: Brian Schiffer, San Francisco, CA (US); Tushar Parlikar, Somerville, MA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 0 days.

(21) Appl. No.: 15/971,306

(22) Filed: May 4, 2018

(65) Prior Publication Data
US 2019/0342973 A1    Nov. 7, 2019

(51) Int. Cl.
| | |
|---|---|
| H05B 37/02 | (2006.01) |
| H05B 47/11 | (2020.01) |
| H01L 25/16 | (2006.01) |
| H05B 45/10 | (2020.01) |
| H05B 45/20 | (2020.01) |
| H05B 47/105 | (2020.01) |

(52) U.S. Cl.
CPC ............ *H05B 47/11* (2020.01); *H01L 25/167* (2013.01); *H05B 45/10* (2020.01); *H05B 45/20* (2020.01); *H05B 47/105* (2020.01)

(58) Field of Classification Search
CPC ........ A61F 13/42; A61F 13/44; A61F 13/505; A61F 13/84; A61F 2013/422; A61F 2013/423; A61F 2013/424; A61F 2013/426; A61F 2013/427; A61F 2013/429

See application file for complete search history.

(56) References Cited

U.S. PATENT DOCUMENTS

| | | |
|---|---|---|
| 3,013,257 A | 12/1961 | Carmelo |
| 3,261,987 A | 7/1966 | Chapin |

(Continued)

FOREIGN PATENT DOCUMENTS

| | | |
|---|---|---|
| CN | 205246547 | 5/2016 |
| CN | 106198538 | 12/2016 |

(Continued)

OTHER PUBLICATIONS

Kästle et al., "A new family of sensors for pulse oximetry", Hewlett Packard Journal 48 (1997): 39-47.

(Continued)

*Primary Examiner* — Jason Crawford
(74) *Attorney, Agent, or Firm* — Kilpatrick Townsend & Stockton LLP

(57) ABSTRACT

Systems and methods for detecting a color of a color changing indicator in the presence of ambient light. A system includes a light source, a photodetector, and a processor. The processor obtains a first measurement of ambient light received from the photodetector while the light source is off. The processor causes the light source to transmit light. The processor obtains a second measurement from the photodetector during the transmission, the second measurement including the ambient light and the pulsed light reflected from an object. The processor determines a color of the color changing indicator by removing an ambient light signal from the second measurement based on the first measurement and therefrom determines a volume of bodily exudate present.

20 Claims, 6 Drawing Sheets

(56) References Cited

U.S. PATENT DOCUMENTS

| | | |
|---|---|---|
| 4,315,159 A | 2/1982 | Niwa et al. |
| 5,079,541 A | 1/1992 | Moody |
| 5,616,140 A | 4/1997 | Prescott |
| 5,654,803 A | 8/1997 | Howard, III et al. |
| 6,147,592 A | 11/2000 | Ulrich et al. |
| 6,287,253 B1 | 9/2001 | Ortega et al. |
| 8,111,165 B2 | 2/2012 | Ortega et al. |
| 8,416,088 B2 | 4/2013 | Ortega et al. |
| 8,628,506 B2 | 1/2014 | Ales, III et al. |
| 8,920,332 B2 | 12/2014 | Hong et al. |
| 2002/0026164 A1 | 2/2002 | Camarero et al. |
| 2004/0022053 A1 | 2/2004 | Sharon et al. |
| 2005/0019508 A1 | 1/2005 | Engel et al. |
| 2005/0195085 A1 | 9/2005 | Cretu-petra |
| 2006/0244614 A1 | 11/2006 | Long |
| 2007/0142796 A1 | 6/2007 | Mosbacher |
| 2007/0142799 A1 | 6/2007 | Ales |
| 2008/0021429 A1* | 1/2008 | Klofta .......... A61F 13/42 604/385.01 |
| 2009/0157025 A1* | 6/2009 | Song .......... A61F 13/42 604/361 |
| 2009/0275908 A1* | 11/2009 | Song .......... A61F 13/42 604/361 |
| 2010/0290948 A1* | 11/2010 | Song .......... A61B 10/007 422/423 |
| 2012/0109087 A1 | 5/2012 | Abraham |
| 2012/0116337 A1* | 5/2012 | Ales .......... A61F 13/42 604/361 |
| 2013/0066289 A1* | 3/2013 | Song .......... A61L 15/56 604/361 |
| 2014/0143183 A1 | 5/2014 | Sigal et al. |
| 2014/0200538 A1* | 7/2014 | Euliano .......... A61F 13/42 604/361 |
| 2015/0164377 A1 | 6/2015 | Vaidhi et al. |
| 2015/0272482 A1 | 10/2015 | Houmanfar et al. |
| 2016/0287074 A1 | 10/2016 | Pradeep et al. |
| 2016/0292576 A1 | 10/2016 | Pradeep et al. |
| 2016/0292584 A1 | 10/2016 | Weinberg et al. |
| 2016/0296144 A1 | 10/2016 | Gaddam et al. |
| 2017/0128274 A1* | 5/2017 | Varga .......... A61F 13/15585 |
| 2017/0215808 A1 | 8/2017 | Shimol et al. |
| 2017/0252225 A1* | 9/2017 | Arizti .......... A61F 13/42 |
| 2017/0348162 A1* | 12/2017 | Arizti .......... A61F 13/42 |
| 2018/0056128 A1 | 3/2018 | Narasimha Rao et al. |
| 2018/0253957 A1 | 9/2018 | Jhangiani et al. |

FOREIGN PATENT DOCUMENTS

| | | |
|---|---|---|
| EP | 2832323 | 2/2015 |
| JP | S61296239 | 12/1986 |
| KR | 1020090041260 | 4/2009 |
| WO | 0100117 | 1/2001 |
| WO | 02063260 | 8/2002 |
| WO | 2007128038 | 12/2007 |
| WO | 2012059832 | 5/2012 |

OTHER PUBLICATIONS

Kim et al., "Miniaturized battery-free wireless systems for wearable pulse oximetry", Advanced functional materials 27.1 (2017): 1604373.

Leonard et al., "Standard pulse oximeters can be used to monitor respiratory rate", Emergency medicine journal 20.6 (2003): 524-525.

PCT/US2019/030684, "International Search Report and Written Opinion", dated Jun. 25, 2019, 11 pages.

International Application No. PCT/US2019/030691, "Invitation to Pay and Partial International Search Report" dated Jul. 30, 2019, 13 pages.

* cited by examiner

COLOR SENSING USING PULSED LIGHT

FIELD

The present application generally relates to color sensing, but more specifically relates to accurately detecting a color of an object in the presence of ambient light. In a particular example, a detected color may be a color of a color changing indicator that changes color based on a presence or a volume of liquid.

BACKGROUND

Color sensing can be used in a variety of applications. For example, color sensing is useful to automatically detect a color of a color changing indicator, a material that changes color following exposure to a specific substance or chemical. Color changing indicators are available to measure different substances, for example, a level of chlorine in a swimming pool or a cleanliness of a surface.

A color changing indicator can also indicate the presence of bodily exudate. But existing solutions for color sensing are insufficient for accurately detecting color in the presence of ambient light. More specifically, ambient light can alter the detected color, causing an erroneous reading. Therefore, while previous solutions may be acceptable for low- or no-light applications such as medical testing, which can be performed in a dark environment such as inside dark equipment, such solutions are inadequate for applications in which ambient light is unavoidable such as testing a color changing indicator in an absorbent article.

Additionally, while other solutions exist for determining a level of bodily exudate in an absorbent article, such solutions are also inadequate. More specifically, solutions that use temperature or humidity sensors alone may provide inaccurate measurements. For example, a humidity sensor may be located too far away from bodily exudate to detect a sudden increase in humidity. Or a temperature sensor may indicate an elevated temperature, but the location of sensing may not be representative of the temperature of the absorbent article overall. Finally, while such solutions are able to detect the presence of bodily exudate, these solutions are unable to detect an amount of bodily exudate present.

SUMMARY

Various examples are described for detecting a color of an object in the presence of ambient light. Additionally, various examples are described for detecting a presence and a volume of bodily exudate in an absorbent article by detecting a color of a color changing indicator.

In an example, a system includes a light source, a photodetector, and a processor. The processor obtains a first measurement of ambient light received from the photodetector while the light source is off. The processor causes the light source to transmit light. The processor obtains a second measurement from the photodetector during the light transmission, the second measurement including the ambient light and the pulsed light reflected from an object. The processor determines a color of the object by removing an ambient light signal from the second measurement based on the first measurement. The processor determines a presence or a volume of bodily exudate present based on the color of the object.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

Features, embodiments, and advantages of the present disclosure are better understood when the following Detailed Description is read with reference to the accompanying drawings.

FIG. 3 comprises FIGS. 3A and 3B, according to certain aspects of the present disclosure.

DETAILED DESCRIPTION

Figure 1:
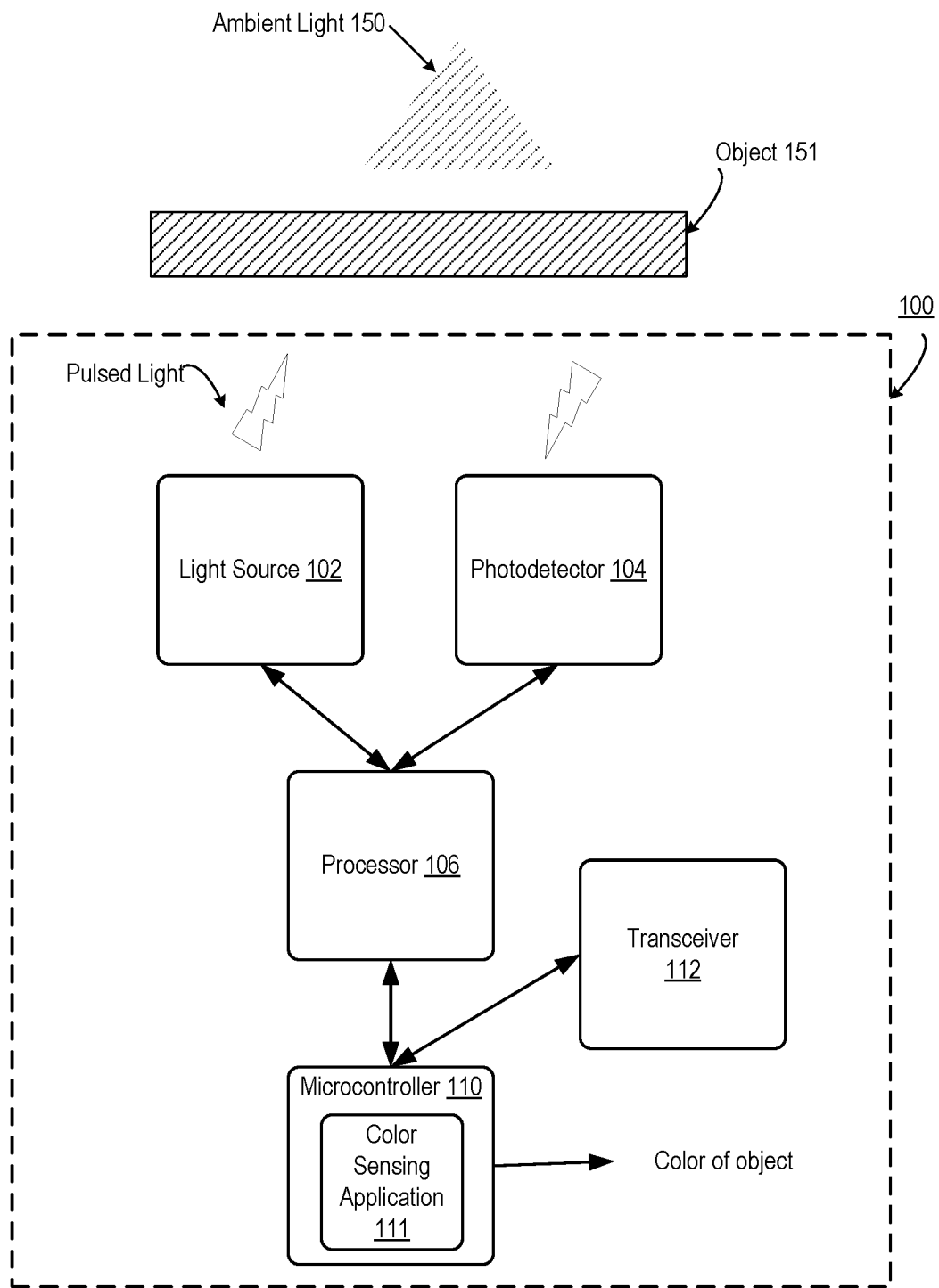
FIG. 1 depicts a block diagram of an example color detection system, according to certain aspects of the present disclosure.

Aspects described herein provide solutions for accurately determining a color of an object, such as a color changing indicator, in the presence of ambient light. More specifically, one example color detection system uses a pulsed light source to accurately detect the color of an object such as a color changing indicator in an absorbent article such as a diaper. This example color detection system includes one or more light sources such as LEDs, one or more photodetectors configured to detect light, and an electronic circuit or device such as a photometric front end or a general purpose processor configurable to receive information about detected color, filter out a contribution of the ambient light, and output a representation of the detected color. Such filtering can be done in the analog domain or the digital domain.

As discussed, existing solutions for detecting color are deficient. Because such solutions are sensitive to ambient light, these solutions cannot reliably detect a color when ambient light is present. Ambient light can vary in intensity or color, for example by being filtered as the light travels through objects, thereby altering the perceived color of the object.

In an example, a color detection system is attached to an infant's diaper and oriented to allow the color detection system to shine light on a portion of the diaper containing a color changing indicator. A color changing indicator can change its color, for example, based on the presence or absence of bodily exudates or in response to some other condition being monitored with respect to the absorbent article. For example, a color changing indicator can be a composition that is coated or printed on the inner surface of a film. Bodily exudates can include urine, feces, menses, blood, etc.

The color detection system includes a photodetector and a light source having a known spectrum that can be used to illuminate the color changing indicator and obtain a sensed value of received light reflected by the color changing indicator, whether from the light source or from ambient light. The color detection system periodically checks the color of the color changing indicator to determine whether bodily exudate is present in the absorbent article, and potentially a quantity of bodily exudate.

To detect bodily exudate, the color detection system uses the photodetector to obtain a first measurement of an intensity of broad-spectrum ambient light with the light source deactivated. Next, the color detection system transmits light from the light source at a particular wavelength and during the pulse, uses the photodetector to obtain a second measurement. Using the second measurement, the color detection system determines an intensity of the light reflected from the color changing indicator under the combination of the pulsed light and the ambient light. The color detection system then filters the ambient light based on the first measurement from the second measurement. Based on the known spectrum of the reflected light, the color detection system determines the color of the color changing indicator and outputs the determined color.

Thus, as illustrated in the example above, the color detection system can illuminate a color changing indicator to accurately determine a presence or absence of a chemical or substance. For example, the color detection system can be used with a color changing indicator that changes color based on a volume of bodily exudate in a diaper, or any other material that changes color in the presence of a substance of interest. Therefore, such a system provides an advantage over existing solutions for detecting and measuring wetness in an absorbent article by more accurately determining a color of a chemical-sensitive color changing indicator. In this manner, the color detection system can effectively determine a presence and amount of bodily exudate in an absorbent article, such as an infant's diaper or a diaper worn by a patient in a hospital or nursing home. Because the color detection system can accurately detect the color of an object even in the presence of ambient light, controlled environments are not needed to obtain accurate results. Further, such an example system can automatically determine whether an infant has wet its diaper and can enable additional applications, such as sending a warning a caregiver to change the diaper.

This illustrative example is given to introduce the reader to the general subject matter discussed herein and the disclosure is not limited to this example. The following sections describe various additional non-limiting examples and examples of color sensing using pulsed light.

FIG. 1 depicts a block diagram of an example color detection system, according to certain aspects of the present disclosure. FIG. 1 includes color detection system 100. Color detection system 100 includes light source 102, photodetector 104, processor 106, and microcontroller 110. In an aspect, only one of the processor 106 and the microcontroller 110 is present. Color detection system 100 can be configured to measure a color of an object 151, including in the presence of ambient light 150.

Ambient light 150 can be any kind of light present in an environment that is not generated by the light source 102, which can include light from natural sources, e.g., sunlight, or artificial light such as light created via incandescent light sources, halogen light sources, light emitting diode ("LED") light sources, fluorescent light sources, laser sources, etc. Even though ambient light can have different color spectra depending on the ambient light source(s) present, color detection system 100 can electronically remove the contribution of such ambient light to light detected by the photodetector and accurately detect the color of the object 151 based on reflected light from the light source 102.

Light source 102 includes one or more light sources operable to shine light on object 151. The light sources can be any suitable artificial light source according to this disclosure, including LEDs, incandescent light sources, or other light sources. Multiple discrete light sources can be implemented individually or via an integrated package that combines multiple individual light sources into a single light source.

Light from light source 102 can be generated at one or more specific wavelengths, or can encompass multiple wavelengths. In an example, light source 102 has three sources of light: red light at wavelength 623 nanometers ("nm"), green light at wavelength 523 nm, and blue light at 455 nm wavelength. Other wavelengths of light may be employed according to different examples, depending on the application, the expected color range of a target object or color changing indicator such as a strip of litmus paper, expected ambient light spectra, or any other suitable factor. In some examples, the light source may be tunable to allow selection of a wavelength or wavelengths of light having a small contribution to the ambient light. For example, if ambient light detected by the photodetector indicates a local or global minimum magnitude at a first wavelength, the color detection system 100 can tune the light source 102 to emit light substantially at the first wavelength.

In this example, the color detection system pulses the light emitted by light source 102 by activating for a short duration, e.g., 1-5 microseconds to 500 milliseconds, called a "pulse width," and then deactivating the light source. Any suitable pulse width may be employed for a particular application. Light source 102 can create a separate pulse for red, blue, and green, and output the corresponding values. For example, a pulse width of 5 microseconds may be advantageous to detect a color of a color changing indicator. Short pulse widths enable the color detection system 100 to pulse and detect different colors of light, e.g., red, green, and blue, in quick succession of each other.

The use of pulsed light enables color detection system 100 to disambiguate the type of light reflected by the object. Specifically, the color detection system 100 can detect and filter the ambient light from detected light that includes light pulsed from the light source 102. In some examples, the color detection system 100 can pulse the light source 102 at regular intervals, e.g., every ten minutes, or in response to an event, such as a user pressing a button on the color detection system or a humidity sensor detecting a humidity level exceeding a threshold. Additionally, the use of pulsed light as compared to constant light can lower the power consumption of the color detection system 100, thereby increasing the amount of time that the color detection system 100 can operate from a battery.

When the light source 102 is pulsed, the detected light at photodetector 104 may be a combination of the ambient light 150 and light from the pulsed light source 102 reflected from the object 151. When the light source 102 is inactive, the light detected by the photodetector 104 is ambient light. By pulsing the light source 102, the color detection system is able to first obtain baseline information about the ambient light spectrum to enable the color detection system to filter light received when the light source 102 is active. Pulsing also allows the color detection system 100 to save power by deactivating the light source 102 when a color measurement is not being taken.

Photodetector 104 receives a light, including light reflected from the object 151, whether ambient light or light emitted by the light source 102, and generates sensor signals based on that received light. Photodetector 104 can be any device that can detect and measure light such as a photodiode, phototransistor, CMOS image sensor, CCD sensor, or a photo-resistor.

Photodetector 104 can detect a wide spectrum of light and output information that indicates the detected light. For example, photodetector 104 can create an electrical output that is proportional to the wavelength of the received light. Photodetector 104 can provide three outputs of an RGB triplet, e.g., a value that corresponds to red, another value for green, and another value for blue.

More specifically, the values of the triplet correspond to the amplitude of light at a range of wavelengths corresponding to a particular color. Therefore, a first value is proportional to an amplitude of red in the received light, a second value is proportional to an amplitude of green in the received light, and a third value is proportional to an amplitude of blue in the received light.

In an aspect, a photodetector 104 can be an array of individual photodetectors. Each photodetector can be configured to measure a color of light. For example, one photodetector measures red, a second photodetector measures blue, and a third photodetector measures green.

Processor 106 is an electronic circuit or device such as a general purpose processor. Processor 106 can operate in the analog domain, digital domain, or both. Processor 106 can discern the true color of the object 151 independent of any ambient light. Processor 106 receives a first output from photodetector 104 that represents the ambient light, for example, an output gathered when the light source 102 is off. Processor 106 receives a second output from photodetector 104 when the light source 102 is pulsed. Processor 106 discerns a difference between the first output and the second output and thereby isolates the color of the object, specifically the color of the reflected light on the object from the pulsed light.

In an aspect, processor 106 receives a level indicating an intensity of broad spectrum light that represents the ambient light, i.e., the point in time that the light source 102 is off, and a level indicating the intensity of for a second point in time at which one of the three colors red, blue, and green, is pulsed. Processor 106 can then disambiguate the contribution of the single pulsed color from the ambient light by comparing the intensity of the ambient light and the intensity with the single pulsed color.

Processor 106 receives a first set red, green, and blue levels from photodetector 104 for a point in time that the light source 102 is off and a second set of red, green, and blue levels from a second point in time that the light source 102 is pulsed. Processor 106 calculates a difference between the level of red between the first and second points in time, thereby calculating a contribution of red, green, and blue levels from the pulsed light.

Processor 106 may be a specialized photometric front end such as Analog Devices® ADPD105, ADPD106, or ADPD107. Processor 106 may be configured to activate light source 102 and measure a signal received by photodetector 104. For example, processor 106 can receive an analog input from photodetector 104, convert the analog input to a digital output by using a analog-to-digital converter (ADC), then store a numerical value indicating the detected color in an internal memory for later comparison with another value.

In this manner, processor 106 may be configured to disambiguate the contribution of the ambient light 150 in the analog domain and output an analog signal or digital value indicative of the color of object 151. For example, the processor 106 can provide an output, such as an RGB triplet value representing the color of object 151.

In an aspect, processor 106 can have multiple detection channels, each corresponding to a pair that of a light source 102 and a photodetector 104. As described further with respect to FIGS. 3A and 3B, each channel can be dedicated to a specific light source-photodetector pair, or a "cell." Each cell can be physically separated so that the processor 106 may measure color in multiple places. Processor 106 can also pulse the light from a particular cell differently from a light from another cell.

Figure 6:
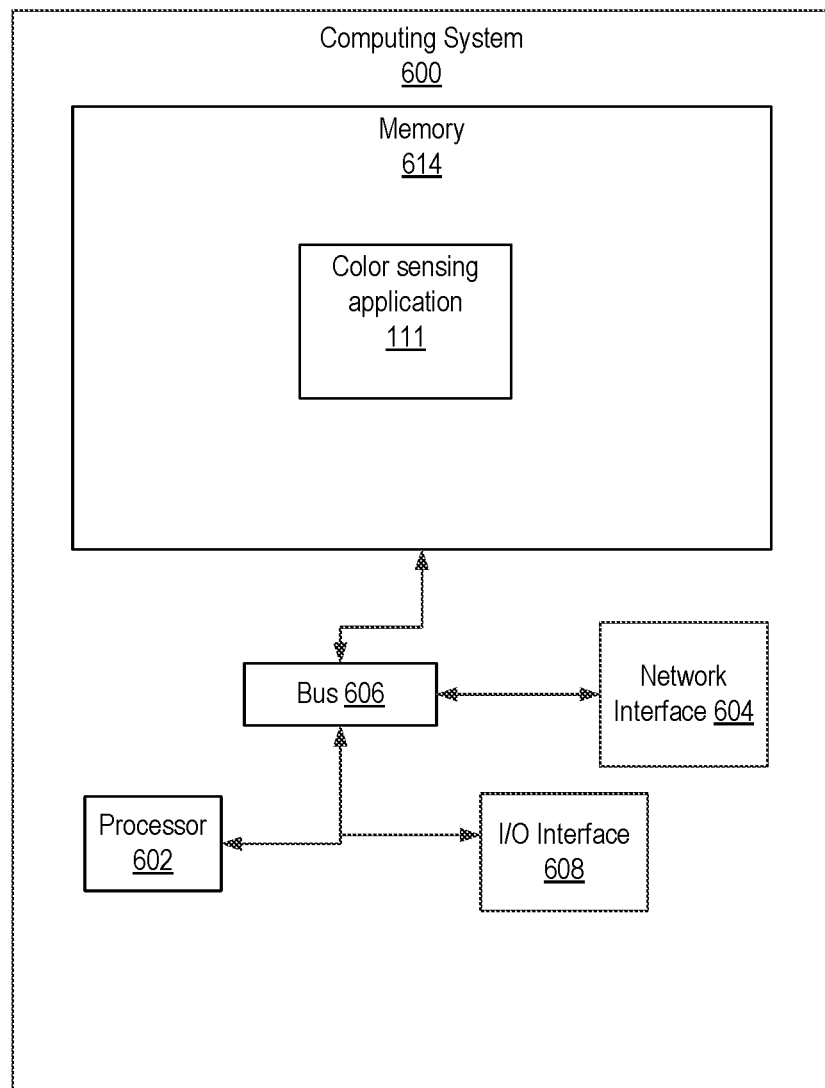
FIG. 6 is a diagram depicting an example computing system for performing functions related to color detection, according to some aspects of the present disclosure.

In an aspect, color detection system 100 also includes a microcontroller 110. Microcontroller 110 can be any controller, processor, application specific integrated circuit or other processing device. An example computing device is shown in FIG. 6. Microcontroller 110 can execute a color sensing application 111 as well as other processor-executable instructions to perform aspects of the present disclosure. The functions of microcontroller 110 can be implemented by processor 106 or vice versa.

Color sensing application 111 can provide additional functionality such as calibration or white balancing for the signal received from light source 102. For example, microcontroller 110 receives a digital input indicating the color of the received light from processor 106. The digital input can include red, green, and blue levels. Color sensing application 111 can convert the red, green, and blue levels to hue, saturation, and lightness/value and perform calculations on the hue, saturation, and lightness/value.

Color sensing application 111 may also calibrate the received color value. For example, color sensing application 111 can retrieve known values such as the detected values when a known color, e.g. represented by a white or gray card or object that is presented to photodetector 104. Color sensing application 111 can adjust the received red, blue, and green levels according to the known calibration values.

In an aspect, microcontroller 110 may be connected to a transceiver 112. Transceiver 112 may communicate according to any suitable wireless protocol, such as Bluetooth, WiFi, near-field communication, etc. Using transceiver 112, microcontroller 110 may transmit the color of the object 151 or, if detecting bodily exudate in an absorbent article, notify an external device that an absorbent article has been soiled. Microcontroller 110 may transmit information to a remote device, such as a smartphone, smartwatch, or other wearable device, or a remote computer, such as a server, e.g., a cloud-based server, for further processing and analysis.

Microcontroller 110 can, via the transceiver 112, transmit the detected color from processor 106 to a remote server, which can map values that represent an expected reflected color from an object to a predicted volume of bodily exudate present in an absorbent article. Such a mapping can be accomplished via a table. For example, a table can contain a mapping between a Red-Blue-Green (RGB) triplet or range of triplets to a predicted volume of bodily exudate.

Object 151 can be a color changing indicator or other material that changes color based on the presence of a chemical. In an aspect, color changing indicator 251 can dissolve in the presence of a liquid such as urine. Accordingly, color detection system 100 can detect a change in color, an appearance of color, or a disappearance of color.

Color detection system 100 can be implemented on a slim material such as plastic or flexible substrate. For example, color detection system 100 can be 1-2 centimeters wide and 2-5 millimeters thick. Color detection system 100 can be made sufficiently small and thin to be placed in an absorbent article such as a diaper, as discussed with respect to FIGS. 2-3. In an example, color detection system 100 can be placed in a diaper that includes a color changing indicator such that the light source 102 and photodetector 104 are aligned with the color changing indicator. Color detection system 100 can also be used to detect the color of any other object such as a color changing indicator that changes color based on the presence of another chemical.

Figure 2:
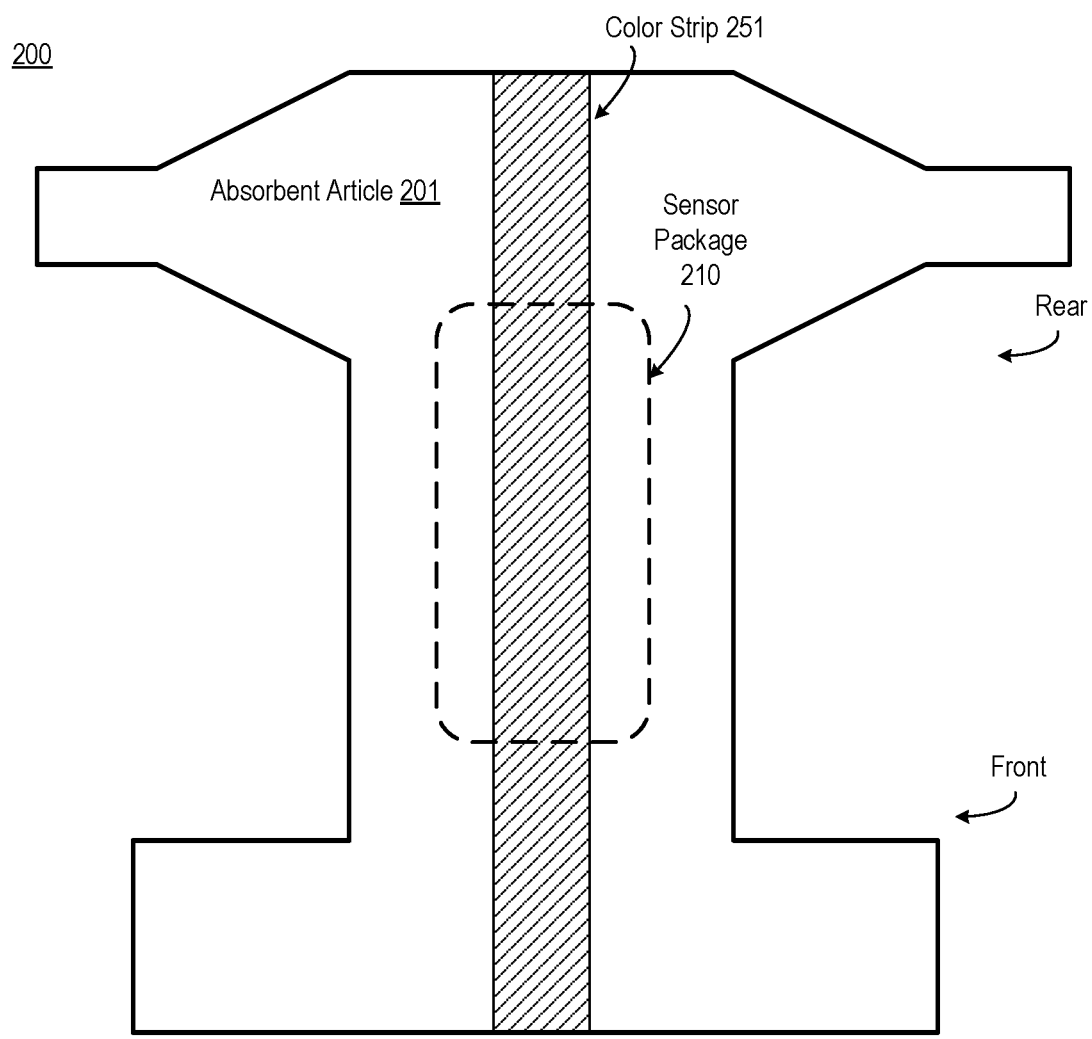
FIG. 2 depicts an absorbent article with color changing indicator and sensing device, according to certain aspects of the present disclosure.

For example and as discussed further with respect to FIG. 2, in one application, color detection system 100 is used to measure the presence of bodily exudate by reading a color changing indicator that changes color based on a presence or volume of a liquid. Exemplary color changing indicators include a pH strip or litmus paper strip that changes color based on detected pH level. Color detection system 100 pulses light onto the color changing indicator and determines the amount of the pulsed light that is reflected.

More specifically, microcontroller 110 is programmed with data points from one or more wavelength-absorbance curves that correspond to different levels of acidity or pH level. By matching an absorbance level of a particular wavelength of light to a particular level of acidity, microcontroller 110 can determine a volume of a particular liquid, e.g., bodily exudate, or a specific pH level. For example, for a wavelength of light of 440 nm, if the measured absorbance is 0.1, then microcontroller 110 determines that a liquid present is basic, and is present in a low volume. In another example, if a measured absorbance of the 440 nm light is 0.3, then microcontroller determines that the liquid is present in high volume due to a high level of acidity. In this manner, microcontroller 110 need not calculate an intermediate pH level, but rather, can map absorbance or reflectance directly to volume of bodily exudate. Microcontroller 110 can determine expected reflectance, i.e., the amount of light at a particular frequency that is expected to be measured by the photodetector 104, based on an absorbance for that frequency.

The microcontroller 110 can retrieve stored calibration values from memory and determine, from the color and the calibration values, the amount of bodily exudate present in the absorbent article. For example, microcontroller 110 can store a table which maps a given value or range of color to a corresponding amount, or volume of bodily exudate present. Microcontroller 110 can have multiple tables, for example, one for each of a set of different color changing indicators. Additionally, the table can be updated, for example, in the event that a different color changing indicator is to be used.

The wavelength of light source 102 may be altered based on a particular application or color changing indicator. For example, a pH color changing indicator may have a greater response at specific wavelengths, and so the light source 102 may be selected or tuned to emit light at such wavelengths. In this manner, by using light sources with particular wavelengths that are better reflected by the color changing indicator, the system can receive stronger reflected pulsed light signals from the object. This can allow the system to more accurately determine the color of the object and therefore more accurately determine a pH value or a corresponding volume based on the determined color. Such accuracy can be particularly valuable when the color values of the color changing indicator do not change linearly with changes in pH.

FIG. 2 depicts an absorbent article with a pH-sensitive color changing indicator and a sensing device, according to certain aspects of the present disclosure. Absorbent article system 200 includes an absorbent article 201, sensor package 210, and color changing indicator 251. In this example, the color detection system 100 of FIG. 1 is implemented on sensor package 210; however any suitable color detection system 100 according to this disclosure may be employed. Further, in some examples, multiple color detection systems, or multiple light sources and photodetectors for a single multiple color detection system, may be employed at different locations within the absorbent article to better detect the presence of bodily exudate at multiple different locations within the absorbent article.

Color changing indicator 251 is shown as extending down the middle of the absorbent article from one end, shown with straps, to the other. Because bodily exudate can be non-uniformly distributed within an absorbent article, placing the color changing indicator 251 down the middle of the absorbent article increases the chance that the color changing indicator 251 will detect bodily exudate in the absorbent article 201. But color changing indicator 251 can be located in different areas of the absorbent article 201. For example, color changing indicator 251 could be located at the front of the absorbent article, or at an edge of absorbent article 201, or any combination of these or other locations.

As can be seen, sensor package 210 is aligned with color changing indicator 251 such that the light source and photodetector elements are positioned over the color changing indicator 251. In some examples, sensor package 210 can be removable from the absorbent article 201. For example, the sensor package 210 can be adhered to the absorbent article 201 to prevent the sensor package 210 slipping, while allowing its removal.

Absorbent article 201 can be any suitable absorbent article such as a common disposable diaper, a reusable cloth diaper, pantiliner, adult diaper, etc. Color changing indicator 251 is a color changing indicator that is designed to change color in response to contact with a substance having a particular property, such as a pH level. For example, color changing indicator 251 can be Bromocresol green, which changes color based on the pH of a liquid to which the color changing indicator has been exposed. The color of the Bromocresol green strip changes with the pH of bodily exudate detected. Other color changing indicators can be used. The detected pH level can be correlated with a volume of bodily exudate, because the pH level changes as the volume of bodily exudate in the absorbent article changes. Accordingly, a lookup table or function may be used to determine a volume for a given pH level, or color of the color changing indicator.

Sensor package 210, further described with respect to FIG. 3, in this example includes the color detection system 100 of FIG. 1 within a flexible, impermeable package. For example, sensor package 210 has a housing that can withstand bodily exudate and feces, and is sufficiently thin as to not cause discomfort to a wearer of the absorbent article. Sensor package 210 may be fabricated with flexible substrate such as a thin plastic, fluroelastomer, or tpsiv.

Sensor package 210 can be placed in the absorbent article in various different ways. In an aspect, sensor package 210 may be removed and inserted in a new absorbent article. Sensor package 210 can be covered with a material or pouch that is washable or can be wiped. For example, sensor package 210 can be inserted into an absorbent article or adhered to the inside of the absorbent article. Sensor package 210 can also be inserted into a pocket or pouch inside the absorbent article. Such a pocket or pouch can be hermetically sealed, for example, in transparent plastic that allows light to pass through. Sensor package 210 can also be permanently attached into an absorbent article and discarded after a one-time use. Sensor package 210 can also be adhered to the outside of the absorbent article via velcro or similar material.

Figure 3A:
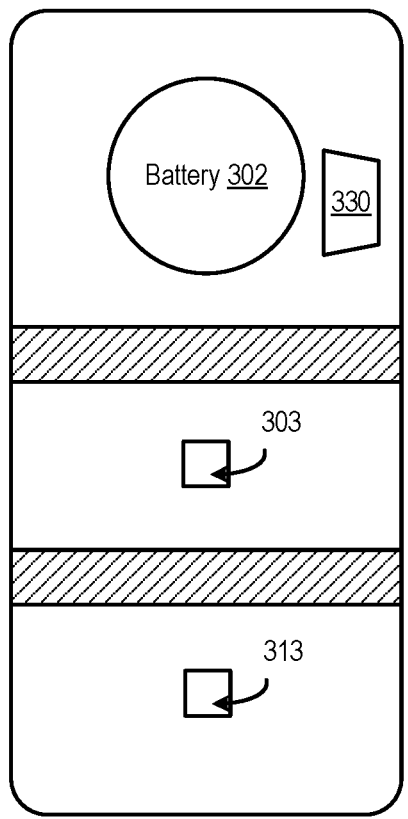
FIG. 3A represents a top side view of an example sensor layout for sensor package 300.
Figure 3B:
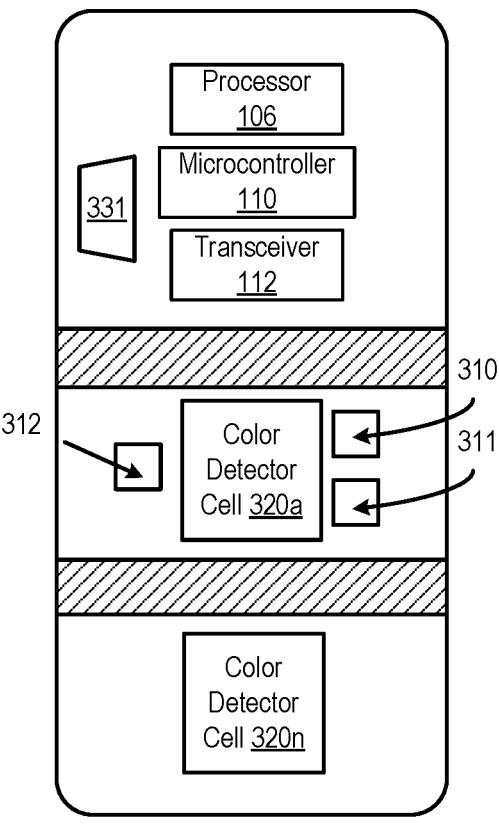
FIG. 3B represents a bottom side view of an example sensor layout for sensor package 300.

FIGS. 3A and 3B depict an example layout of a sensor system that can be placed in or on the outer surface of an absorbent article, according to certain aspects of the present disclosure. FIG. 3A represents a top-down view of an example sensor layout for sensor package 300. FIG. 3B represents a bottom-up view of an example sensor layout for sensor package 300. The bottom is the side that is positioned to face and align with the color changing indicator 251. Sensor package 300 can be used in conjunction with the absorbent article 201 depicted in FIG. 2, i.e., as sensor package 210. The sensor system shown in FIG. 3, when placed in an absorbent article, by detecting a color of a color changing indicator in the absorbent article, can determine a presence and volume of bodily exudate present in the absorbent article in conjunction with an internal system such as microcontroller 110 that can map color to bodily exudate volume.

Sensor package 300 includes a battery 302 and one or more color detector cells 320a-n. Sensor package 300 may also include a switch 303, two electrical connectors 330-331, a volatile organic compound ("VOC") sensor 310, a temperature sensor 311, a humidity sensor 312, an additional ambient light sensor 313, processor 106, microcontroller 110, or transceiver 112. Additional ambient light sensor 313 can be used in conjunction with the photodetectors to improve or augment the light detecting capability of sensor package 300. Some aspects may not include all of the components described above, or include variants thereof.

In addition, the sensor package 300 can cause an alarm, such as an audible beep, based on a threshold level of bodily exudate being detected. Accordingly, sensor package 300 can include a speaker or other audio output device. Sensor package 300 can also cause a transmission of an alert to another device, for example, operated by a caretaker. In another aspect, sensor package 300 can transmit an alert to another device. Sensor package 300 can include a transmitter or transceiver capable of transmitting a radio signal to an external device. Color sensing application 111 operating on microcontroller 110 can also log events, such as when bodily exudate is detected, to memory for later transmission to a caregiver.

Sensor package 300 can include one or more color detector cells 320a-n. For example, multiple color detector cells 320a-n can increase the ability of the sensor package 300 to detect changes in bodily exudate across the absorbent article. Because bodily exudate may not be distributed uniformly in an absorbent article, the color of color changing indicator 251 may not change uniformly along the length of the color changing indicator. Additionally, the presence of multiple color detector cells 320a-n enables a calculation of multiple data points to more accurately estimate the total load.

Each color detector cell 320a-n includes a light source such as an LED and a photodetector such as a photodiode. In some aspects, as discussed further with respect to FIG. 4, a color detector cell may include multiple light sources or multiple photodetectors. Each color detector cell 320a-n detects light reflected by object 151 such as a color changing indicator 251, such as ambient light or pulsed light from the light source(s). The output of each color detector cell 320a-n is provided to a processor 106. The output of processor 106 can be provided to microcontroller 110. In some examples, each color detector cell 320a-n may have a dedicated processor 106, while in some examples, multiple color detector cells 320a-n may be connected to a common processor 106.

Sensor package 300 can include a switch 303 to activate or deactivate the sensor package 300. The switch 303 can be any suitable switch, such as a rocker-style on/off switch that connects the battery 302 to the electronics in sensor package 300 such as the color detectors 320a-n and sensors 310-313. Switch 303 can also be a pushbutton switch that activates power from battery 302 to sensor package 300 for a period of time. Sensor package 300 can be configured to automatically turn off to save battery power. In an aspect, in conjunction with microcontroller 110, sensor package can be activated remotely. For example, a user can prompt an external device with a voice command, which causes the external device to transmit a request for a status of the absorbent article to the microcontroller 110 via a wireless connection, or a request to turn on or turn off the sensor package 300.

Sensor package 300 can include one or more electrical connectors such as electrical connectors 330-331. Electrical connectors 330 and 331 can be used to debug the sensor package 300, calibrate the sensor package 300, reset the sensor package 300 to factory settings, upgrade software on the sensor package 300, etc.

As discussed with respect to FIG. 1, processor 106 can discern a color of an object such as a color changing indicator. Microcontroller 110 can execute an application such as color sensing application 111 that can perform calibration of the detected color value. Transceiver 112 can notify an external device if the sensor package 300 detects the presence of bodily exudate in an absorbent article.

In an aspect, sensor package 300 can also include a VOC sensor 310. VOC sensor 310 can detect the presence of volatile organic compounds such as feces from a bowel movement or VOCs present in blood. In conjunction with data obtained from color detector cells 320a-n, the VOC sensor 310 can provide additional information to microcontroller 110 based on one or more detected volatile organic compounds.

In an aspect, sensor package 300 can also include a temperature sensor 311. Temperature sensor 311 can detect heat from substances such as bodily exudate. In conjunction with data obtained from color detector cells 320a-n, the temperature sensor 311 can provide additional information such as a temporary increase in temperature to microcontroller 110. Because a notification of a temporary increase in temperature can indicate a presence of bodily exudate, such information can improve the accuracy and reliability of the detection.

In another aspect, sensor package 300 can also include a humidity sensor 312. Humidity sensor 312 can detect the presence of humidity, e.g., from bodily exudate. In conjunction with data obtained from color detector cells 320a-n, humidity sensor 312 can provide additional information such as a notification of a temporary increase in humidity to microcontroller 110. Because a temporary increase in temperature can indicate a presence of bodily exudate, such information can improve the accuracy and reliability of the detection.

In a further aspect, sensor package 300 can also include additional ambient light sensor 313. Additional ambient light sensor 313 can be placed, as shown, oriented away from the color detector cells 320a-n to more accurately detect the ambient light. In conjunction with data obtained from color detector cells 320a-n, additional ambient light sensor 313 can provide additional information to microcontroller 110 that allows microcontroller 110 to better disambiguate the contribution of ambient light to the color of the color changing indicator. Additional ambient light sensor 313 can also provide the microcontroller 110 with information as to whether an infant who is wearing an absorbent article in which the sensor package 300 is placed is in a dark room. For example, sensor package 300 can provide an indication or a notification to a caregiver that the light in a baby's room is either on or off.

As discussed, sensor package 300 can include multiple color detector cells 320a-n. The presence of more than one color detector cell 320a-n allows for increased accuracy and reliability. For example, one detector cell 320a-n could become obstructed by an object, rendering detected values from that cell unusable, or because bodily exudate may not be evenly distributed in an absorbent article, and therefore not evenly distributed on a color changing indicator, the use of more than one detector cell 320a-n increases the probability that one of the detector cells 320a-n detects bodily exudate. In this manner, additional color detector cells 320a-n help add robustness in the case that any single cell 320a-n fails or is misaligned. Further, the additional of more sells 320a-n can provide additional local information that may help estimate total load. In contrast, fewer cells 320a-n can simplify the overall system architecture and may also lower power consumption.

In another example, in a system with three detector cells 320a-c, if one detector cell 320a returns a color measurement that is inconsistent with detector cells 320b and 320c, then microcontroller 110 can ignore the measurements from detector cell 320a.

Figure 4:
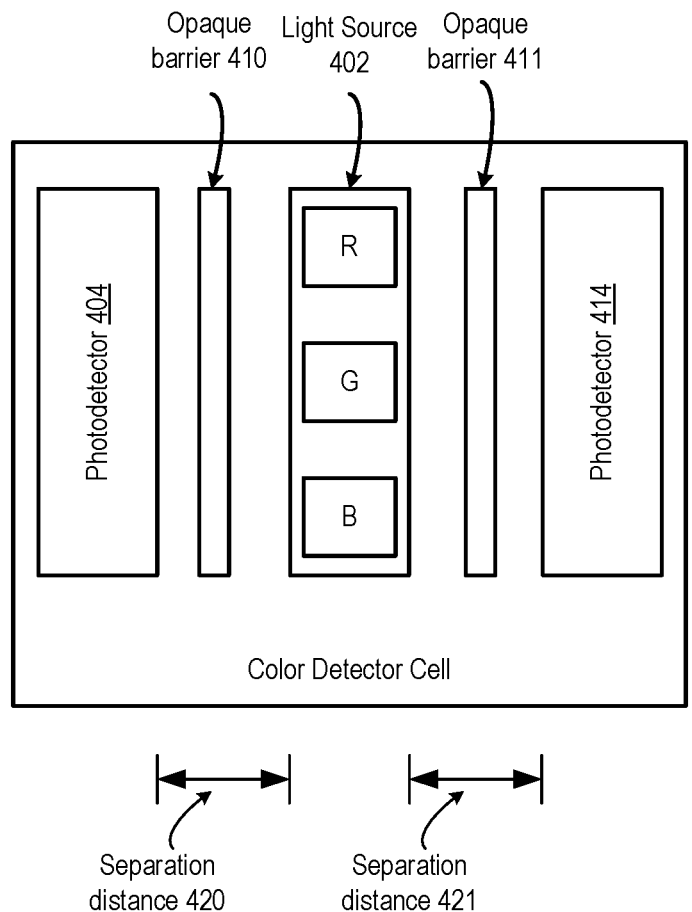
FIG. 4 depicts an example color detector cell configuration, according to certain aspects of the present disclosure.

FIG. 4 depicts an example color detector cell configuration, according to certain aspects of the current disclosure. As discussed, a sensor system such as sensor package 300 includes one or more color detection cells 320a-n. FIG. 4 shows an example color detector cell 400 in more detail.

Color detector cell 400 includes two photodetectors, photodetector 404 and photodetector 414, light source 402, opaque barrier 410, and opaque barrier 411. Light source 402 can be any suitable light source according to this disclosure. As shown, light source 402 includes a red, a blue, and a green light source, though different numbers and types of light sources 402 may be used according to different examples, which can allow the light sources can be turned on and off, i.e., pulsed, separately. Pulsing the light sources 402 that emit different colors separately allows color detector cell 400 to tailor the light output to a specific wavelength of light. For example, a particular color changing indicator may be more responsive to a specific wavelength of light at a specific pH level.

Photodetectors 404 and 414 can be any suitable photodetector according to this disclosure. Photodetectors 404 and 414 are connected to the processor 106. A separation distance 420 between the light source 402 and the photodetector 404 and separation distance 421 between light source 402 and photodetector 414 can be adjusted based on the application. In particular, the closer the light source 402 and a photodetector 404 or 414 are together, the greater the portion of light received at the photodetectors from the light source 402 (and less from ambient light 150). As an example only, separation distance 420 and separation distance 421 can be adjusted from 0.1 mm to 2 mm in separation. Other distances and configurations are possible. As a distance increases, all else being equal, the intensity of the light from the light source received at the photodetector decreases. Additionally, as the distance increases, the focal area being measured increases. As the distance decreases, the sensor is more focused on a smaller area directly under the sensor.

As shown, two photodetectors 404 and 414 are used. Photodetectors 404 and 414 can be positioned to be parallel to each other. In this configuration, the combination of photodetectors 404 and 414 provides a stronger output signal to the processor 106 than otherwise. Using more than one photodetector also provides an advantage in that error can be reduced if the sensor system is misaligned with respect to the object, e.g., color changing indicator 251.

Color detector cell 400 can include one or more opaque barriers 410-411 positioned between the light source 402 and the photodetectors 404, 414. The opaque barriers 410-411 reduce the amount of light from light source 402 that travels directly to the photodetector 404 without reflecting off of the object. Opaque barriers 410-411 can be poron or similar material. In an aspect, the photodetectors 404 or 414 can include such an opaque barrier, or an opaque housing of the photodetector 404 or 414 can be extruded in such a manner that the opaque housing is located between the LED and photodiodes. In an aspect, the opaque barriers 410-411 are omitted to simplify the design.

Figure 5:
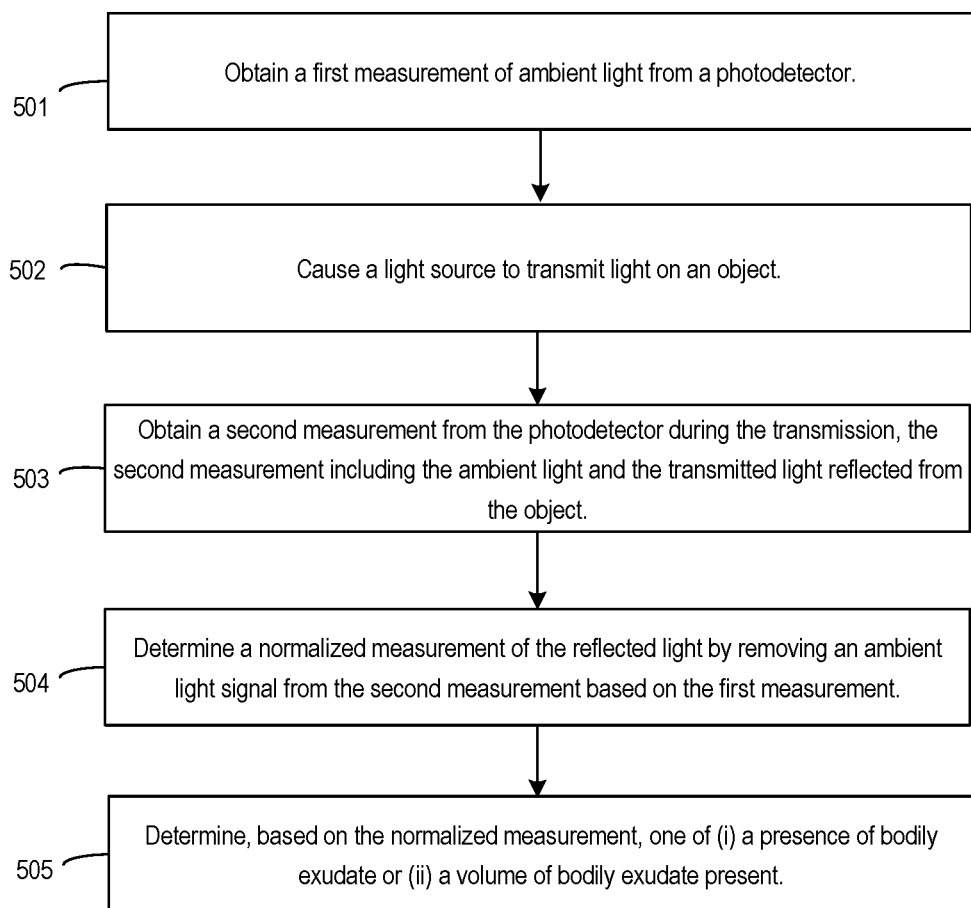
FIG. 5 is a flowchart that describes method of detection of color, according to certain aspects of the present disclosure.

FIG. 5 is a flowchart that describes a method of detecting color, according to certain aspects of the present disclosure. The example method of FIG. 5 will be described with respect to the color detection system 100 of FIG. 1; however, any suitable color detection system according to this disclosure may be employed according to different examples.

At block 501, the color detection system 100 obtains a first measurement of ambient light received from the photodetector. Photodetector 104 detects the ambient light present and outputs a representation of the color of the light or a representation of an intensity of broad-spectrum light that is present. For example, photodetector 104 can create an electrical output that is proportional to the wavelength or the intensity of the received light. In an aspect, the photodetector 104 can provide three outputs that each correspond to red, green, or blue: a first that is proportional to an amplitude of red in the received light, a second that is proportional to an amplitude of green in the received light, a third that is proportional to an amplitude of blue in the received light.

Photodetector 104 provides the first measurement of light to the processor 106. In this example, the first light measurement is taken while a light source 102 is off and represents ambient light reflected from the object 151. The first light measurement can represent an intensity of broad-spectrum light.

The blocks of method 500 can be performed by sensor package 300 of FIG. 3 placed in an absorbent article as described with respect to absorbent article system 200 of FIG. 2. Because sensor package 300 can include one or more color detector cells 320a-n, in an aspect in which more than one detector cells 320a-n are present, sensor package 300 can measure a level of ambient light at multiple photodetectors. The photodetector in each cell 320a-n can independently perform the blocks 500-505.

At block 502, the color detection system 100 causes the light source to transmit of light on an object. More specifically, processor 106 activates light source 102 for a predetermined pulse time interval. In this example, the color detection system 100 only includes one light source 102. But in some examples, multiple light sources may be pulsed simultaneously or individually. For example, aspects using sensor package 300 may include more than one color detector 320a-n. The light source in each color detector 320a-n may be pulsed separately or together with the other light sources.

At block 503, the color detection system 100 obtains a second measurement from the photodetector during the transmission, the second measurement including the ambient light and the transmitted light reflected from the object. Processor 106 obtains a second measurement of light during the time interval that the pulse from light source 102 is on. The second measurement includes the ambient light and the light from the pulsed light source 102. In an aspect such as sensor package 300, the photodetector in each cell 320a-n each obtains a second measurement of light. Color detection system 100 uses the first and second measurements to determine the color of an object.

In an aspect, the color detection system 100 can obtain more than one measurement with the ambient light and the pulsed light present. Processor 106 can average the multiple measurements together to form one single measurement that can be used as a second measurement.

At block 504, the color detection system 100 determines a normalized measurement of the reflected light by removing an ambient light signal from the second measurement based on the first measurement. Removal can be performed in the analog domain or the digital domain.

For example, processor 106 can remove the first measurement of light from the second measurement of light by filtering in the analog domain. For example, the processor 106 subtracts the first measurement, representing the ambient light, from the second measurement, representing the ambient light combined with the reflected light from light source 102. The result of the subtraction is the light reflected from the object 151, such as a color changing indicator.

Processor 106 can operate in the digital domain. For example, processor 106 converts the first measurement into a digital or numeric representation of the red, green, and blue levels. Processor 106 converts the second measurement into a digital or numeric representation of the red, green, and blue levels. Processor 106 computes a new red level by subtracting the first measurement from the red level of the second measurement, a new green level by subtracting the first measurement from the green level of the second measurement, and a new blue level by subtracting the first measurement from the blue level of the second measurement. The new red, green, and blue levels represent the color of the light reflected from the object.

At block 505 the color detection system 100 determines, based on the normalized measurement, one of (i) a presence of bodily exudate or (ii) a volume of bodily exudate present. Processor 106 outputs the color of the object detected at block 505 to the microcontroller 110. The color sensing application 111, executing on the microcontroller, receives the color value from processor 106 and uses a data structure such as a table to determine a presence of bodily or a value representing a volume of bodily exudate. Microcontroller 110 may store several tables, for example, one table which facilitates the mapping of a color on a color changing indicator such as Bromocresol green, to a pH level, and another table that facilitates the mapping of a color changing indicator to a measure or presence of a volume of bodily exudate.

Additionally, as discussed, color sensing application 111 can perform color calibration. Color sensing application 111 can convert the red, green, and blue levels to hue, saturation, and lightness/value and perform calculations on the hue, saturation, and lightness/value. Color calibration can be implemented via a table. For example, for a given triple of red, green, and blue, adjust the values by certain amount. Color calibration can also be performed in a different domain such as hue, saturation, and lightness, or hue, saturation, and value.

In an aspect, color sensing application 111 can determine the presence of bodily exudate in the presence of movement. For example, sensor package 300 caused to be moved by an infant at the same time as color sensing application 111 is performing measurements. In this case, color sensing application can use a known responsiveness of the absorbent article or color strip at two or more different wavelengths of light to determine a presence of exudate. In an example color sensing application 111 can detect that a response to red light is greater than a response to blue light even in the presence of motion.

In a further aspect, color sensing application 111 can detect when an absorbent article is not attached to an infant. In this case, the sensor responsiveness changes below a threshold, which is detected by color sensing application 111.

FIG. 6 is a diagram depicting an example computing system for performing functions related to color detection, according to some aspects of the present disclosure. Some or all of the components of the computing system 600 can belong to the microcontroller 110 of FIG. 1 or the processor 106 of FIG. 1. For example, the color sensing application 111 may operate on the computing system 600. The computing system 600 includes one or more processors 602 communicatively coupled to one or more memory devices 614. The processor 602 executes computer-executable program code, which can be in the form of non-transitory computer-executable instructions, stored in the memory device 614, accesses information stored in the memory device 614, or both. Examples of the processor 602 include a microprocessor, an application-specific integrated circuit ("ASIC"), a field-programmable gate array ("FPGA"), or any other suitable processing device. The processor 602 can include any number of processing devices, including one.

The memory device 614 includes any suitable computer-readable medium such as electronic, optical, magnetic, or other storage device capable of providing a processor with computer-readable instructions or other program code. Non-limiting examples of a computer-readable medium include a magnetic disk, a memory chip, a ROM, a RAM, an ASIC, optical storage, magnetic tape or other magnetic storage, or any other medium from which a processing device can read instructions. The instructions may include processor-specific instructions generated by a compiler or an interpreter from code written in any suitable computer-programming language, including, for example, C, C++, C#, Visual Basic, Java, Python, Perl, JavaScript, and ActionScript.

The computing system 600 may also include a number of external or internal devices such as input or output devices. For example, the computing system 600 is shown with an input/output ("I/O") interface 608 that can receive input from input devices or provide output to output devices. A bus 606 can also be included in the computing system 600. The bus 606 can communicatively couple one or more components of the computing system 600 and allow for communication between such components.

The computing system 600 executes program code that configures the processor 602 to perform one or more of the operations described above with respect to FIGS. 1-5. The program code of the color sensing application 111, which can be in the form of non-transitory computer-executable instructions, can be resident in the memory device 614 or any suitable computer-readable medium and can be executed by the processor 602 or any other one or more suitable processor. Execution of such program code configures or causes the processor(s) to perform the operations described herein with respect to the microcontroller 110. In additional or alternative aspects, the program code described above can be stored in one or more memory devices accessible by the computing system 600 from a remote storage device via a data network. The microcontroller 110 and any processes can use the memory device 614. The memory device 614 can store, for example, additional programs, or data used by the applications executing on the processor 602 such as the color sensing application 111.

The computing system 600 can also include at least one network interface 604. The network interface 604 includes any device or group of devices suitable for establishing a wired or wireless data connection to one or more data networks. Non-limiting examples of the network interface 604 include an Ethernet network adapter, WiFi network, Bluetooth, or Bluetooth Low Energy (BLE), a modem, or the like. The computing system 600 is able to communicate with one or more other computing devices or computer-readable data sources via a data network using the network interface 604.

Numerous specific details are set forth herein to provide a thorough understanding of the claimed subject matter. However, those skilled in the art will understand that the claimed subject matter may be practiced without these specific details. In other instances, methods, apparatuses, or systems that would be known by one of ordinary skill have not been described in detail so as not to obscure claimed subject matter.

Unless specifically stated otherwise, it is appreciated that throughout this specification discussions utilizing terms such as "processing," "computing," "calculating," "determining," and "identifying" or the like refer to actions or processes of a computing device, such as one or more computers or a similar electronic computing device or devices, that manipulate or transform data represented as physical electronic or magnetic quantities within memories, registers, or other information storage devices, transmission devices, or display devices of the computing platform.

The system or systems discussed herein are not limited to any particular hardware architecture or configuration. A computing device can include any suitable arrangement of components that provide a result conditioned on one or more inputs. Suitable computing devices include multi-purpose microprocessor-based computer systems accessing stored software that programs or configures the computing system from a general purpose computing apparatus to a specialized computing apparatus implementing one or more aspects of the present subject matter. Any suitable programming, scripting, or other type of language or combinations of languages may be used to implement the teachings contained herein in software to be used in programming or configuring a computing device.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure.

That which is claimed is:

1. A system for determining a presence of bodily exudate in an absorbent article, the system comprising:
    a light source;
    a photodetector;
    a processor configured to:
        obtain a first measurement of ambient light received from the photodetector while the light source is off;
        cause the light source to transmit light on an object;
        obtain a second measurement from the photodetector during the light transmission, the second measurement comprising a measurement of the ambient light and the light reflected from the absorbent article;
        determine a normalized measurement of the reflected light by removing an ambient light signal from the second measurement based on the first measurement;
        retrieve, from a memory, a stored color calibration value; and
        determine, based on the normalized measurement and the stored color calibration value, a color of the object.

2. The system of claim 1, wherein the second measurement comprises separate measurements of red light, green light, and blue light and wherein determining the normalized measurement comprises determining a separate intensity of red light, green light, and blue light.

3. The system of claim 1, wherein the light is transmitted at a particular wavelength that is determined based on a responsiveness of the object to different wavelengths of light.

4. The system of claim 1, wherein the object comprises a printed or coated region comprising a Bromocresol green color changing indicator.

5. The system of claim 1, where the stored color calibration value is determined using a white colored object and the determining the color of the object comprises performing white level correction.

6. The system of claim 1, further comprising a temperature sensor, wherein the processor is further configured to determine, based on a measure of temperature received from the temperature sensor and the color of the object, a presence of moisture in the absorbent article.

7. The system of claim 1, further comprising a humidity sensor, wherein the processor is further configured to determine, based on a measure of humidity received from the humidity sensor and the color of the object, a presence of moisture.

8. The system of claim 1, further comprising a volatile organic compound sensor, wherein the processor is further configured to:
    retrieve, from the volatile organic compound sensor, a signal indicative of a presence of a volatile organic compound; and
    determine, based on the signal, a presence of fecal matter.

9. The system of claim 1, wherein the object is a color changing strip.

10. The system of claim 1, wherein the processor is further configured to detect, based on the color of the object, one or more of (i) a presence of bodily exudate or (ii) a volume of bodily exudate present in the absorbent article.

11. A method for determining a color of an object, the method comprising:
    obtaining a first measurement of ambient light received from a photodetector while a light source is off;
    causing the light source to transmit light on an object;
    obtaining a second measurement from the photodetector during the light transmission, the second measurement comprising a measurement of the ambient light and the light reflected from the object;
    obtaining a normalized measurement of the reflected light by removing an ambient light signal from the second measurement based on the first measurement;

retrieving, from a memory, a stored color calibration value; and determining, based on the normalized measurement the stored color calibration value, a color of the object.

12. The method of claim 11, wherein the second measurement comprises separate measurements of red light, green light, and blue light, wherein determining the color comprises determining a separate intensity of red light, green light, and blue light.

13. The method of claim 11, further comprising:

retrieving from a memory, a set of coefficients that map color to a volume of bodily exudate; and determining, from the set of coefficients, a volume of bodily exudate corresponding to the color.

14. A sensor package comprising:

a thin flexible substrate adaptable for placement in or on an absorbent article configured for receiving bodily exudate;

a light source configurable to provide transmitted light to a surface or a layer of the absorbent article;

a photodetector configurable to obtain a first measurement of returned light when the light source is off and a second measurement of returned light when the light source is on;

a processor configured to:

obtain a first measurement of ambient light received from the photodetector while the light source is off;

cause the light source to transmit light;

obtain a second measurement from the photodetector during the transmitted light, the second measurement comprising the ambient light and the light reflected from an object on the absorbent article; and determine a color of the object by removing an ambient light signal from the second measurement based on the first measurement; and a microcontroller configured to:

receive, from the processor, the color of the object;

retrieve from a memory, a set of coefficients that map the color of the object to a volume of bodily exudate; and determine, from the set of coefficients and a stored color calibration value, a presence of bodily exudate in the absorbent article; wherein the light source, photodetector, and processor are disposed on the thin flexible substrate.

15. The sensor package of claim 14, wherein the second measurement comprises separate measurements of red light, green light, and blue light, wherein determining the color comprises determining a separate intensity of red light, green light, and blue light, and wherein the presence of bodily exudate present in the absorbent article is determined on the separate intensities.

16. The sensor package of claim 14, where the stored color calibration value is determined using a white colored object.

17. The sensor package of claim 14, wherein the processor is further configured to cause the light source to emit a wavelength and amplitude of light based on a responsiveness of the object to different wavelengths of light.

18. The sensor package of claim 14, further comprising a temperature sensor, wherein the microcontroller is further configured to determine, based on a measure of temperature received from the temperature sensor and the color of the object, a presence of moisture.

19. The sensor package of claim 14, further comprising a humidity sensor, wherein the microcontroller is further configured to:

receive, from the humidity sensor, a measurement of humidity; and determine, based on the measure of humidity and the color of the object, a presence and volume of moisture.

20. The sensor package of claim 14, further comprising a volatile organic compound sensor, wherein the microcontroller is further configured to:

receive, from the volatile organic compound sensor, a measurement of volatile organic compound; and determine, based on the measure of volatile organic compound and the color of a color changing indicator, a presence and volume of moisture.

* * * * *